(12) United States Patent
Sano et al.

(10) Patent No.: US 9,408,982 B2
(45) Date of Patent: Aug. 9, 2016

(54) SAFETY SYRINGE PREVENTING THE NEEDLE STORAGE MECHANISM FROM BEING OPERATED BEFORE USE

(75) Inventors: Minoru Sano, Osaka (JP); Yoshihisa Hama, Osaka (JP)

(73) Assignee: Nipro Corporation, Osaka (JP)

( * ) Notice: Subject to any disclaimer, the term of this patent is extended or adjusted under 35 U.S.C. 154(b) by 1259 days.

(21) Appl. No.: 11/991,807

(22) PCT Filed: Sep. 12, 2006

(86) PCT No.: PCT/JP2006/318072
§ 371 (c)(1),
(2), (4) Date: May 10, 2010

(87) PCT Pub. No.: WO2007/032352
PCT Pub. Date: Mar. 22, 2007

(65) Prior Publication Data
US 2010/0312197 A1    Dec. 9, 2010

(30) Foreign Application Priority Data
Sep. 13, 2005 (JP) ................................. 2005-265815

(51) Int. Cl.
*A61M 5/32* (2006.01)
*A61M 5/315* (2006.01)
*A61M 5/50* (2006.01)

(52) U.S. Cl.
CPC ........... *A61M 5/322* (2013.01); *A61M 5/31501* (2013.01); *A61M 5/31505* (2013.01); *A61M 2005/31506* (2013.01); *A61M 2005/31508* (2013.01); *A61M 2005/3231* (2013.01); *A61M 2005/5073* (2013.01)

(58) Field of Classification Search
CPC .................. A61M 2005/3224; A61M 5/322; A61M 2005/31508; A61M 2005/3231; A61M 2005/3223; A61M 5/5066; A61M 2005/31506; A61M 2005/5073; A61M 5/31501; A61M 5/31505
USPC ......... 604/220, 110, 240, 195, 187, 111, 181, 604/192, 197, 198, 218, 228
See application file for complete search history.

(56) References Cited

U.S. PATENT DOCUMENTS

| 5,533,970 A | * | 7/1996 | Berger et al. ............. 604/110 |
| 6,796,969 B1 | * | 9/2004 | Andersson ............... 604/198 |
| 6,821,266 B2 | * | 11/2004 | Knepshield et al. ....... 604/110 |
| 2001/0021821 A1 | * | 9/2001 | Wang et al. .............. 604/110 |
| 2006/0052748 A1 | * | 3/2006 | Coelho et al. ............ 604/110 |

* cited by examiner

Primary Examiner — Bhisma Mehta
Assistant Examiner — Brandy S Lee
(74) Attorney, Agent, or Firm — Kubovcik & Kubovcik

(57) ABSTRACT

To provide a syringe with a needle storage mechanism in which the needle storage mechanism is not activated before use. A safety syringe including an injection barrel 1 having a connecting portion 11 at the distal end and an opening at the proximal end thereof, a needle assembly B having an injection needle 5 and a needle base 6 fixed to the proximal end of the injection needle 5 and being connected to the connecting portion 11, a gasket 2 provided liquid-tightly and slidably in the injection barrel, a plunger 3 being connected to the proximal end of the gasket 2 and joining means 21 provided at the distal portion of the gasket 2 or the plunger 3, and joined means 61 provided at the proximal portion of the needle base 6, wherein a joint preventing means 90 which prevents the joining means 21 and the joined means 61 from being joined unintentionally before use, and allows joining to each other when in use is provided.

1 Claim, 5 Drawing Sheets

SAFETY SYRINGE PREVENTING THE NEEDLE STORAGE MECHANISM FROM BEING OPERATED BEFORE USE

TECHNICAL FIELD

The present invention relates to a syringe provided with a needle storage mechanism for preventing puncture by mistake after use.

BACKGROUND ART

In the related art, a drug solution is administered to a patient by an injection syringe, and then the injection needle is recapped with a protector before being discarded. However, so-called puncture by mistake such that medical workers such as nurses pick their own finger with an injection needle having patient's blood attached thereon by mistake at the time of recapping, or the recapping protector is separated from the needle for some reason and workers who handle the injection needle pick themselves with the used injection needle has been a problem. Through such puncture by mistake, the medical worker may be infected with bacteria or virus existing on the injection needle, whereby the medical worker may be affected by a disease.

In order to avoid the problem of puncture by mistake as described above, tools which are capable of safely disposing used injection needles without touching the used injection needles, for example, a needle discard container as shown in Patent Document 1, have been proposed, and there are medical institutions which employ this discard container.

However, in the case where emergency medical procedures are required for a patient such as in critical care centers, or in places where the discard container can hardly be installed, it is impossible to discard the injection needles using the discard container.

Therefore, there is proposed a structure of an injection syringe which allows the injection needle to be discarded safely without puncture by mistake. For example, there is an injection syringe provided with a tube outside an injection barrel. The tube is capable of engaging the distal end of the injection barrel and of sliding toward the distal end of the injection barrel, and has an inner diameter which is substantially equivalent to the outer diameter of the injection barrel. This injection syringe is capable of avoiding a puncture by sliding the tube toward the distal end of the injection barrel and covering the portion from the distal end of the injection barrel to beyond the distal end of the needle with the tube after use (Patent Document 2).

There is also an injection syringe configured to be capable of storing the needle in the injection barrel. After a patient is administered medicine, a plunger is connected with the needle by pushing the plunger into the distal end of an injection barrel, so that the plunger and the needle are operable. The needle is retracted into the injection barrel by pulling the plunger, and then the needle is completely stored in the injection barrel in an inoperable state by separating the plunger, thereby being discarded safely (Patent Document 3).
Patent Document 1: JP-A-1-242064
Patent Document 2: JP-A-5-337182
Patent Document 3: JP-A-2003-205035

DISCLOSURE OF INVENTION

Problem to be Solved by the Invention

However, the injection syringe described in Patent Document 2 employs an outer tube which is larger than the injection barrel, and hence the manufacture cost is increased. In addition, since the distal end of the outer tube is widely open after use, there is still a probability of puncture by mistake or contact with blood when the user touches the opening or near the opening with the worker's finger. When the outer tube is slid rearward after use, the injection needle is exposed again. Therefore, the puncture by mistake may not be prevented completely. The injection syringe described in Patent Document 3 has a plunger which is operable freely in the axial direction. Therefore, before use, in particular when connecting the needle to the injection barrel or when drawing drug solution from ampoule or the like into the injection syringe, the plunger may be pushed into the distal end of the injection barrel and hence the plunger may be connected with the needle, whereby the needle storage mechanism is operated. Consequently, the needle and the plunger are joined to each other before using the injection syringe, and hence the injection syringe cannot be used at all. Therefore, it is necessary that a structure of the needle storage mechanism is such that the injection needle is prevented from being exposed again and is not operated before use.

It is an object of the invention to provide a syringe with a needle storage mechanism in which the needle storage mechanism is not operated before use.

Means for Solving the Invention

The inventors have achieved this invention by finding as follows. A plunger is prevented from being pushed into the distal end of an injection barrel before use by accidental force, and hence operation by mistake such that the needle storage mechanism is operated before use is avoided especially when attaching the needle to the injection barrel, so a state in which the syringe is brought into an unusable state without being used is avoided by providing:
(1) A safety syringe including: an injection barrel having a connecting portion at the distal end and an opening at the proximal end thereof; a needle assembly having an injection needle and a needle base fixed to the proximal end of the injection needle and being connected to the connecting portion; a gasket provided liquid-tightly and slidably in the injection barrel; a plunger being connected to the proximal end of the gasket; joining means provided at the distal portion of the gasket or the plunger; and joined means provided at the proximal portion of the needle base; wherein a joint preventing means is provided which prevents the joining means and the joined means from being joined unintentionally before use, and allows joining to each other when in use.
(2) The safety syringe according to (1), wherein the joint preventing means is a movement preventing member detachably attached between the proximal end of the injection barrel and the proximal end of the plunger, and one end of the joint preventing means is in contact with the proximal end of the injection barrel and the other end is in contact with the proximal end of the plunger so as to prevent the joining means from moving toward the joined means when being attached.
(3) The safety syringe according to (2), wherein the movement preventing member is attached to the proximal end portion of the plunger.
(4) The safety syringe according to (3), wherein the movement preventing member is attached to the proximal end portion of the injection barrel.
(5) The safety syringe according to (1), wherein the joint preventing means is a separable projection which is provided at a midsection of the plunger and is in contact with the proximal end of the injection barrel before separation, so as to prevent the joining means from moving toward the joined means.

(6) The safety syringe according to (1), wherein the joint preventing means is a separable projection provided on the proximal end portion of the injection barrel and which is in contact with the proximal end of the plunger before separation so as to prevent the joining means from moving toward the joined means.

(7) The safety syringe according to (1), wherein the joint preventing means is an elastic projection which is provided at the proximal end portion of the plunger and is in contact with the proximal end of the injection barrel before use so as to prevent the joining means from moving toward the joined means and is positioned within the range of the inner diameter of the injection barrel when in use.

(8) The safety syringe according to (1), wherein the joint preventing means is an elastic projection which is provided at the proximal end portion of the injection barrel and comes into contact with the proximal end of the plunger before use so as to prevent the joining means from moving toward the joined means and is positioned out of the outer diameter of the midsection of the plunger when in use.

(9) The safety syringe according to (1), wherein the joint preventing means includes an engaging portion provided in the interior of the proximal end of the injection barrel and an engaged portion provided at the midsection of the plunger, and the engaging portion and the engaged portion are brought into engagement before use and into disengagement when in use.

Advantage of the Invention

As described above, the syringe of the invention is provided with the joint preventing means, and hence the gasket does not come into contact with the distal end of the injection barrel unless the joint preventing means is released, and hence the joining means and the joined means are not joined to each other. Therefore, the gasket and the needle body are prevented from being connected with each other and becoming unusable before the injection syringe is used. In addition, since the sliding movement of the gasket in the axial direction is enabled by releasing the joint preventing means, the needle storage mechanism can be operated, and the needle stored into the injection barrel after use, so that puncture by mistake is avoided. In addition, the needle is prevented from being exposed again by separating the plunger and the gasket, so the syringe of the invention is suitably used for medical practice.

DESCRIPTION OF THE REFERENCE NUMERALS AND SIGNS

Figure 1:
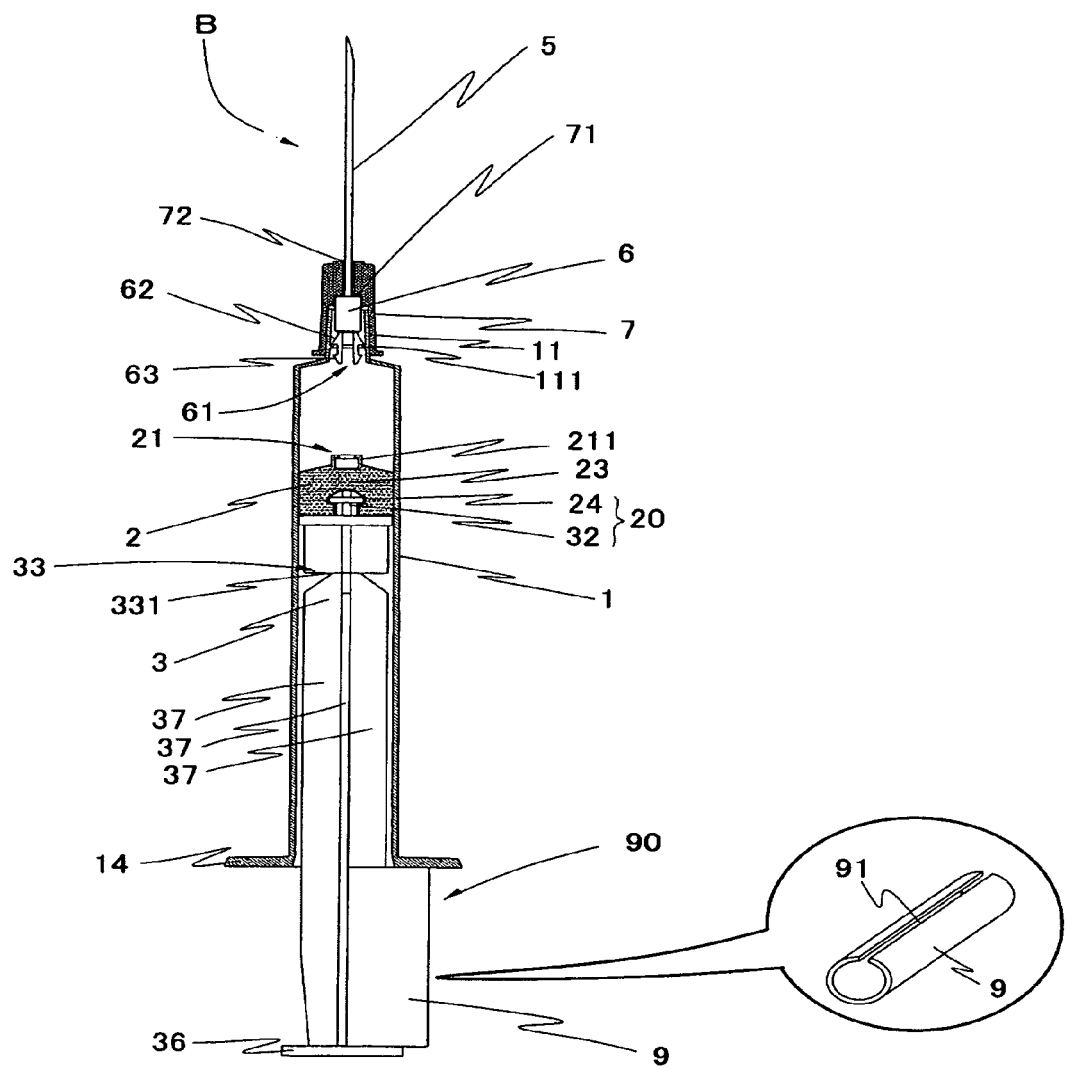
FIG. 1 is vertical cross-sectional view of an embodiment of a safety syringe according to the invention.

B needle assembly
1 injection barrel
11 connecting portion
111 rib
12 in-tube rib
13 annular rib
14 finger mount portion
15 drug solution
2 gasket
20 coupled portion
21 joining means
211 tube body
23 bulkhead portion
24 fitting recess
3 plunger
32 fitting projection
33 separating means
331 notch
34 projecting portion
341 separating portion
35 elastic projection
36 flange
37 vertical rib
38 L-shaped vertical rib
5 injection needle
6 needle base
61 joined means
62 upper claws
63 lower claws
7 needle base lid member
71 needle base fitting portion
72 hole
9 distal direction movement preventing member
90 joint preventing means
91 slit

BEST MODE FOR CARRYING OUT THE INVENTION

Referring now to the drawings, a syringe of the invention will be described. However, the invention is not limited to embodiments shown in the drawings.

Figure 2A:
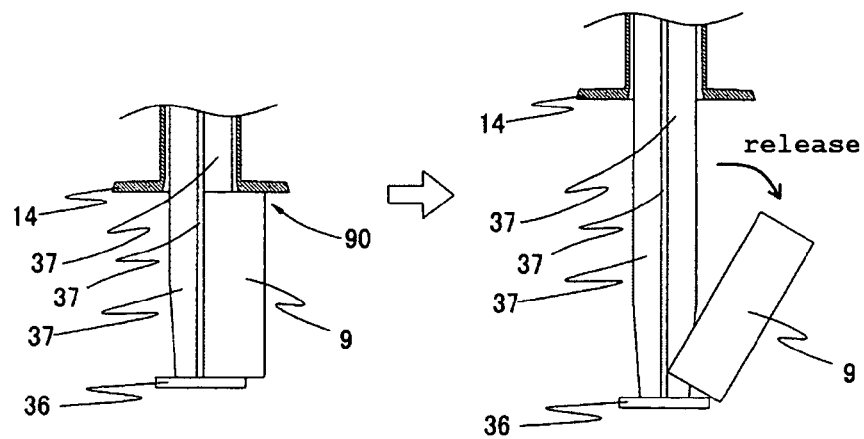
FIGS. 2(a) to (c) are partially enlarged vertical cross-sectional views of other embodiments showing joint preventing means which relate a gasket to a needle body.
Figure 2B:
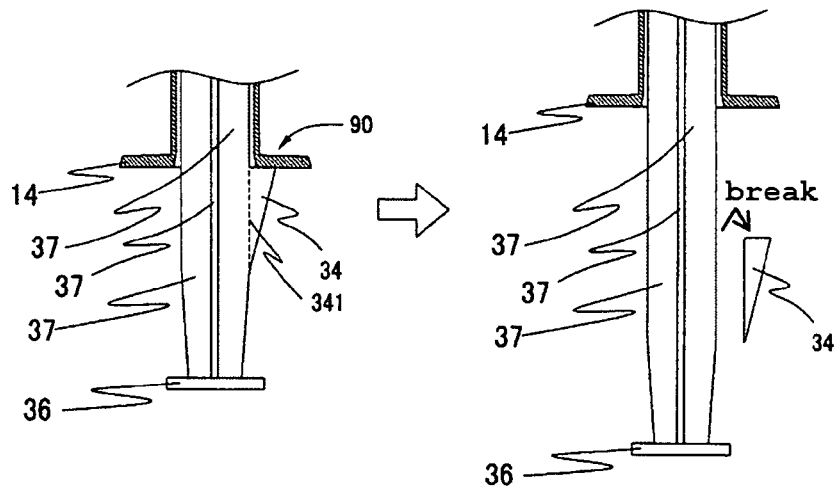
Figure 2C:
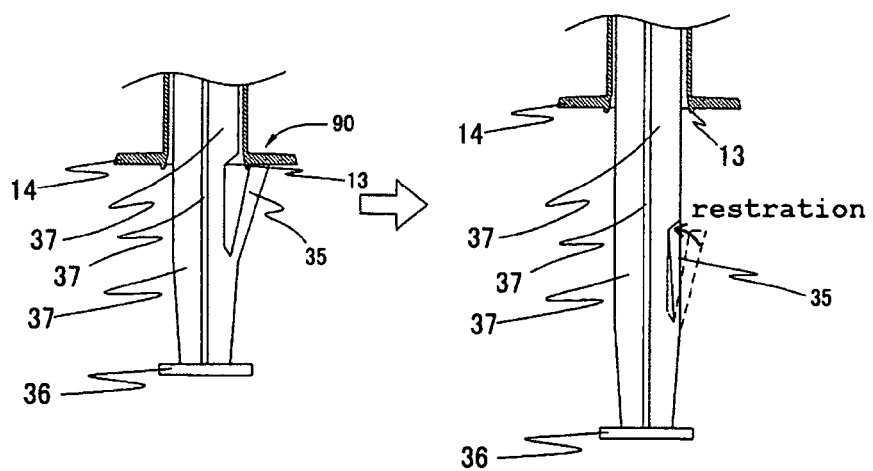
Figure 3:
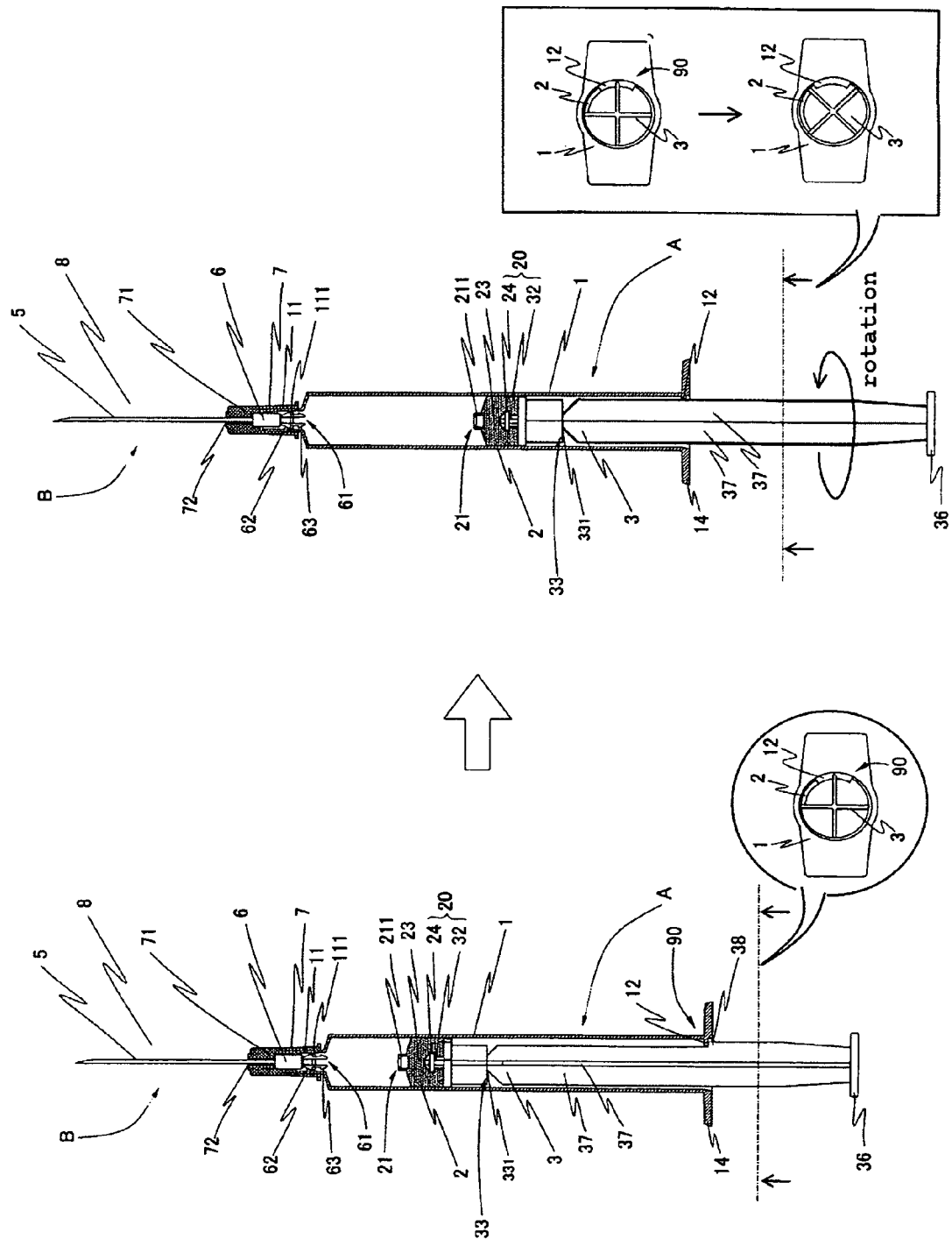
FIG. 3 is a partially enlarged vertical cross-sectional view of still another embodiment of joint preventing means between the gasket and the needle body.
Figure 4:
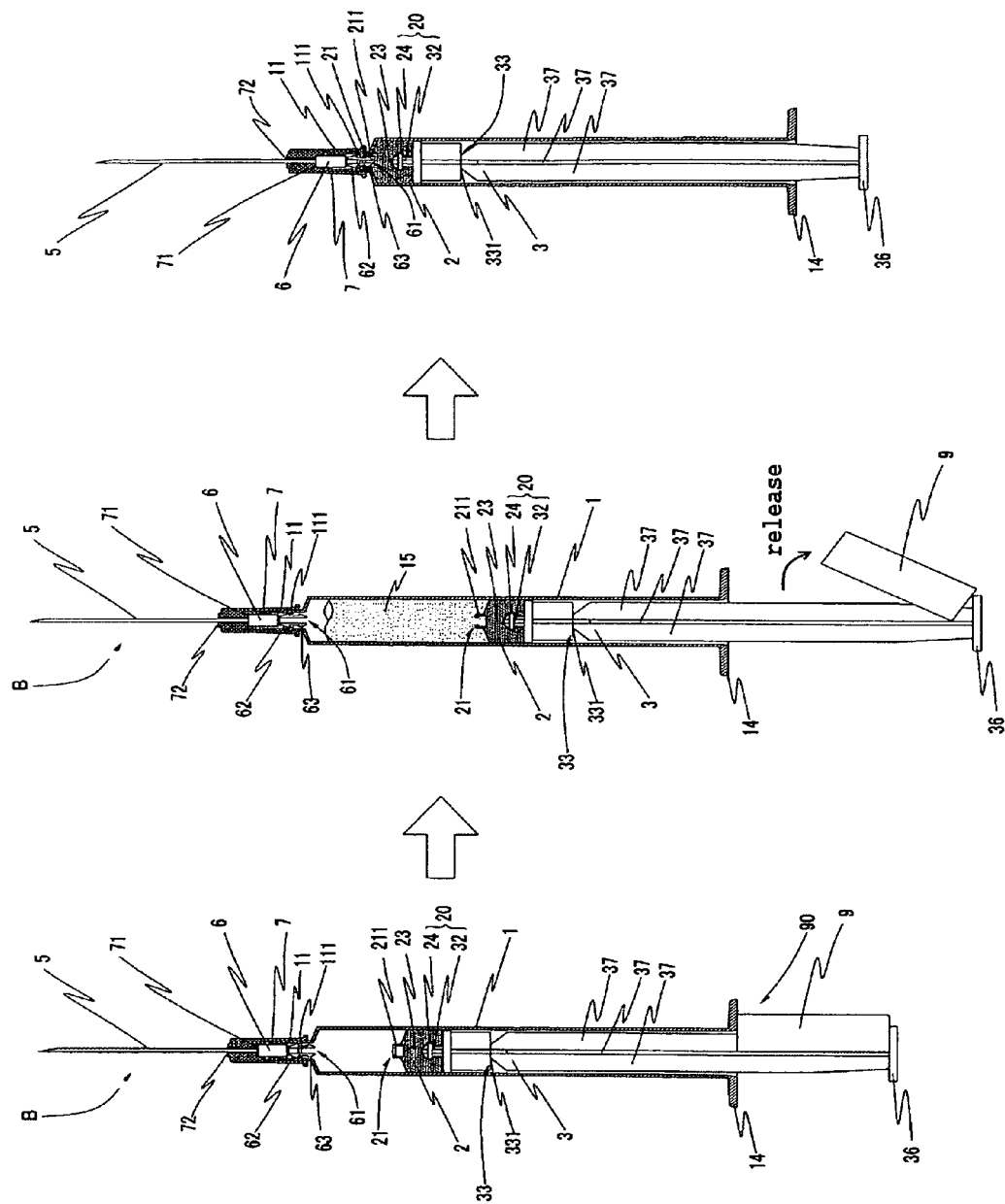
FIG. 4 is a vertical cross-sectional view showing a method of usage by drawing of drug solution into the safety syringe shown in FIG. 1.
Figure 5:
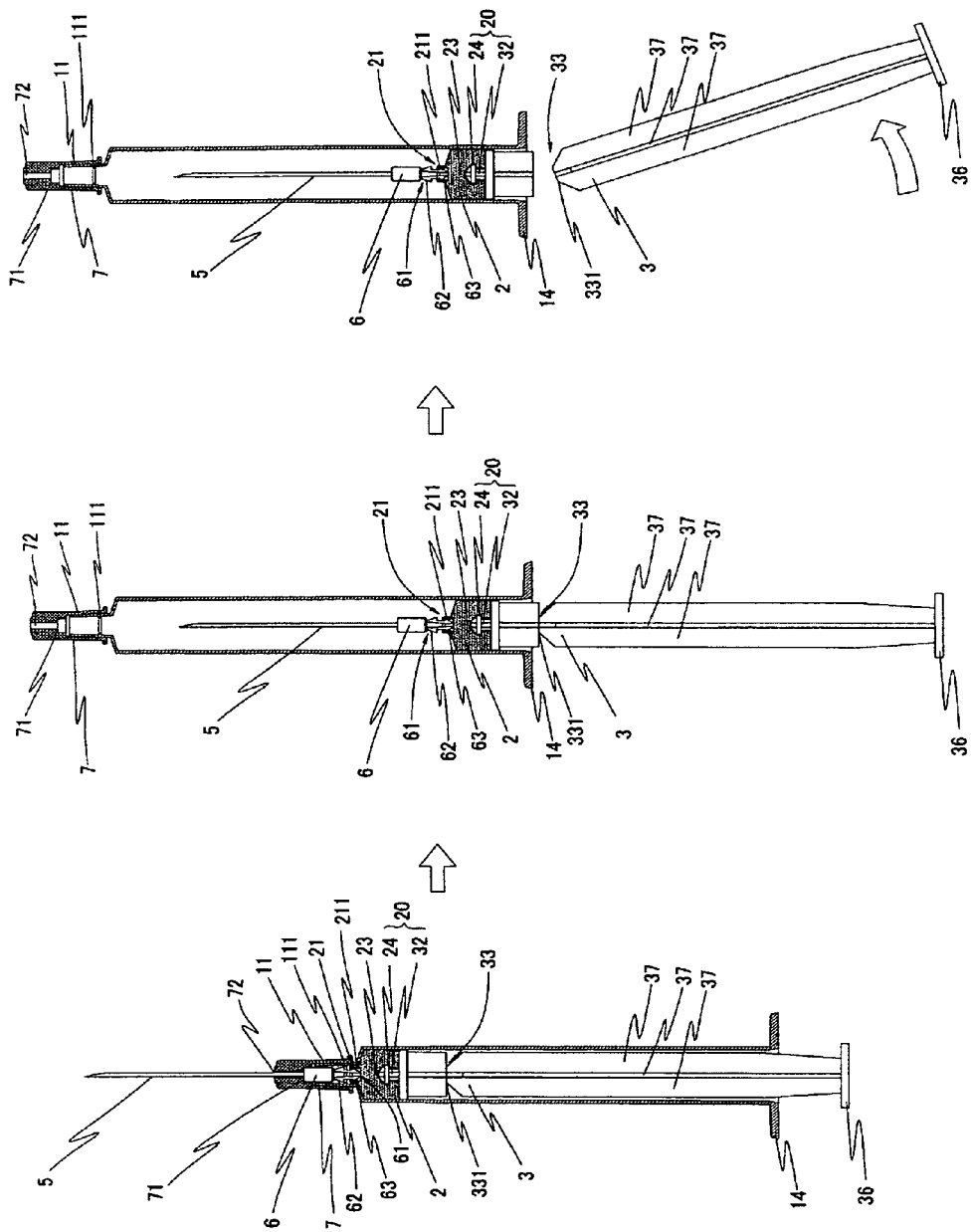
FIG. 5 is a vertical cross-sectional view illustrating a process from after having administered drug solution in the safety syringe shown in FIG. 1 until the safety syringe is discarded.

FIG. 1 is a vertical cross-sectional view of a safety syringe according to an embodiment of the invention. FIGS. 2(a) to (c) and FIG. 3 are partially enlarged vertical cross-sectional views of joint preventing means which relate a gasket to a needle body of other embodiments. FIG. 4 is a vertical cross-sectional view illustrating a method of usage until drawing of drug solution into the safety syringe shown in FIG. 1. FIG. 5 is a vertical cross section illustrating a process after having administered the drug solution in the safety syringe shown in FIG. 1.

FIG. 1 illustrates a safety syringe including a needle assembly B, an injection barrel 1, a gasket 2 and a plunger 3. The needle assembly B includes a needle body having an injection needle 5 and a needle base 6, a needle base lid member 7, and a needle cover 8. The needle body has the injection needle 5 at the distal end, and the distal end of the needle base 6 having a flow channel which communicates with the injection needle and having a larger diameter than that of the injection needle 5 is secured to the proximal end of the injection needle 5. The needle base 6 is provided with joined means 61 having upper claws 62 and lower claws 63 at the left and right of the proximal end thereof. The needle base lid member 7 includes a hole 72 at the distal end thereof. The hole 72 allows passage of the injection needle 5 and prevents passage of the needle base 6. A needle base fitting portion 71 on which the needle base 6 fits is provided on the proximal end side of the hole 72, and the proximal end of the needle base fitting portion 71 is fitted to a connecting portion 11 of the injection barrel 1. The injection needle 5 is inserted through the hole 72, and the distal end of the needle base 6 is fitted to the needle base fitting portion 71, so the distal end side of the needle base lid member 7 is closed. The injection barrel 1 has a hollow and substantially cylindrical shape, and includes the connecting portion 11 having a flow channel at the distal end thereof and an opening at the proximal end thereof. A rib 111 is formed in the connecting portion 11, the needle base lid member 7 of the needle assembly B is connected to the connecting portion 11, and the upper claws 62 of the needle assembly B engage the rib 111. The gasket 2 is stored in the injection barrel 1 so as to be liquid-tight and slidable in the direction of axis of the injection barrel 1. The distal end of the gasket 2 is integrally equipped with a tube body 211 having an annular rib on the inner wall of the distal end as a joining means 21 and the proximal end of the gasket is equipped with a fitting recess 24. The tube body 211 formed at the distal end of the gasket is arranged coaxially with the connecting portion 11 formed on the injection barrel 1. A bulkhead portion 23 is formed between the tube body 211 and the fitting recess 24, and the tube body 211 and the fitting recess 24 as a connecting portion 20 is partitioned by the bulkhead portion 23, so the interior of the injection barrel and the outside are kept in a liquid-tight state. The plunger 3 having a fitting projection 32 which can be fitted to the fitting recess 24 at the distal end thereof is attached to the gasket 2. The plunger 3 is equipped with a notch 331 as a separating means 33 for separating the plunger 3 from the gasket 2. A detachable distal direction movement preventing member 9 which is in contact at both surfaces thereof with a proximal surface of a finger mount portion 14 of the injection barrel 1 and a distal surface of a flange 36 of the plunger and having a slit 91 capable of being fitted to vertical ribs 37 of the plunger 3 is fitted to the proximal end side of the plunger 3, thereby functioning as joint preventing means 90.

The needle body is prevented from moving toward the distal end by the distal end of the needle base fitted into the needle base fitting portion 71 of the needle base lid member and toward the proximal end by the upper claws 62 engaged with the rib 111, so that the needle body is prevented from easily separating or moving. Therefore, the possibilities that the needle is retracted into the injection barrel when being pricked into a human body, and that the needle body is separated from the injection syringe when pulling out the needle from the human body and hence the needle body staying pricked into the human body are avoided. Also, the slit 91 of the distal direction movement preventing member 9 is fitted to the vertical ribs 37 of the proximal end portion of the plunger and the both surfaces of the distal direction movement preventing member are in contact with the proximal surface of the finger mount portion 14 of the injection barrel 1 and the distal surface of the flange 36 of the plunger, so that movement toward the distal end of the injection barrel is hindered. Furthermore, the space in the injection barrel is prevented from communicating with the outside by providing the bulkhead portion between the joining means of the gasket and the coupled portion, so that there is no probability of leakage of drug solution in the injection barrel to the outside and of contamination of the drug solution.

Since the diameter of the needle base 6 of the needle assembly B is larger than that of the injection needle 5, it is impossible that the needle body penetrates trough the hole 72 at the distal end of the needle base lid member 7, and the distal end of the needle base 6 is not easily separated from the needle base fitting portion 71. Therefore, even when the needle assembly B exists independently, the needle body is not improperly separated from the needle base lid member 7.

The structure of the coupled portion 20 between the gasket 2 and the plunger 3 is not specifically limited as long as the gasket 2 and the plunger 3 can be coupled, and a structure in which the coupling between the gasket 2 and the plunger 3 is not releasable is also applicable. The plunger 3 and the gasket 2 may be coupled to each other by forming the fitting recess 24 at the proximal end of the gasket 2, forming the fitting projection 32 which is fitted to the fitting recess of the gasket 2 at the distal end of the plunger 3 and fitting them, or may be coupled by forming a female thread on the gasket and a male thread which can be screwed into the female thread of the gasket 2 on the plunger 3, and screwing. In the case where screwing is employed as the coupled portion, the coupled portion is also able to serve as a separating means and hence it is not necessary to additionally provide a separating means to the plunger. Therefore, the plunger does not have a fragile portion, and hence the plunger is robust. In the case where a fitting is employed as the coupled portion, manufacturing is simple. In addition, in order to couple the plunger 3 with the gasket 2, a structure in which the joining means is equipped with the plunger and penetrates the gasket is applicable.

The separating means 33 may be of any structure as long as the gasket 2 and the plunger 3 are separable and, for example, a structure having the notch 331 to break the plunger 3 and a structure having cuts and hinges alternately in the form of dotted lines to twist off the plunger are also applicable. Even through the connecting portion 20 serves as the separating means 33, for example, the gasket 2 is connected to the plunger by screwing, other separating means 33 which are not the connecting portion 20 can be equipped. Since the gasket coupled with the needle body is able to be separated from the plunger after use by providing the separating means, the needle body and the gasket may be stored in the injection barrel in a state of immovability, and hence the injection syringe is safely discarded without exposing the needle.

The injection barrel 1 may be equipped with a stopper for preventing the gasket 2 from coming off from the opening at the proximal end of the injection barrel 1. The stopper may be of any shape and material as long as drawing of drug solution into the injection barrel and administration of the drug solution to the patient are not impeded, the needle body integrated with the gasket can be stored completely in the injection barrel, and the gasket 2 is prevented from dropping off the injection barrel 1. For example, an annular rib may be integrally-formed near the opening of the injection barrel 1, or a stopper which is a separate member from the injection barrel 1 may be formed and fitted into the injection barrel 1. By providing the stopper, the gasket is prevented from dropping off the injection barrel before use and, in particular, the gasket integrated with the needle body after use is prevented from dropping off the injection barrel, so injury by puncture is prevented during the disposal of the injection syringe.

The gasket 2 is made of a rubber elastic member, and resins which have characteristics of rubber elasticity and are used for normal syringe gaskets may be employed. Since the rubber elastic member has a liquid-tight property, butyl rubber, silicone rubber, thermoplastic elastomer, and silicone elastomer are applicable. The injection barrel 1 and the plunger 3 are not specifically limited as long as it can be used for the syringe, and known materials may be employed. However, thermoplastic resin is preferable since it is molded easily.

The material and the shape of the joining means 21 of the gasket 2 are not specifically limited, as long as the joining means 21 does not break, does not separate from the gasket 2 during use, and can be joined with the joined means 61. And hence the joining means 21 and the gasket 2 are integrally formed, and the joining means 21 and the gasket 2 are formed separately and the joining means 21 is fitted into the gasket 2. In a case where the joining means 21 is formed separately from the gasket 2, the method of attachment of the joining means 21 to the gasket 2 is not specifically limited as long as it does not come off during use. In the case where the joining means is formed integrally with the gasket, manufacturing is simple and the probability of separation between the joining means and the gasket is avoided. In the case where the joining means and the gasket are formed separately, for example, since the joining means may be made of thermoplastic resin or the like, the joining means and the joined means are joined easily in comparison with the rubber elastic member, and a firm joint is achieved. In addition, in order to couple the plunger 3 with the gasket 2, a structure in which the joining means is equipped with the plunger and penetrates the gasket is applicable.

The material, the shape and the structure of a joint preventing means 90 are not specifically limited as long as the gasket is not connected to the needle body before use and, activation of joint prevention during use or hindrance to sliding movement of the gasket are not caused. As shown in FIG. 2(a), movement of the gasket toward the distal end of the injection barrel may be impeded by fitting the distal direction movement preventing member 9 formed of a different member from the plunger 3 and the injection barrel 1 to the plunger 3. Alternatively, as shown in FIG. 2(b), the movement of the gasket 2 toward the distal end of the injection barrel may be impeded by providing the plunger 3 with a separable projection 34 which comes in contact with the proximal surface of the finger mount portion 14 of the injection barrel. Further alternatively, as shown in FIG. 2(c), the movement of the gasket 2 toward the distal end of the injection barrel may be impeded by providing an elastic projection 35 having a free end on the distal end side on the plunger 3 and providing an annular rib 13 on the proximal surface of the finger mount portion 14 of the injection cylinder and engaging the elastic projection 35 and the annular rib 13 or, as shown in FIG. 3, the movement of the gasket 2 toward the distal end of the injection barrel may be impeded by providing an in-tube rib 12 on the inner wall of the injection barrel 1 as an engaging portion and providing an L-shape vertical rib 38 on the plunger 3 as the engaged portion, and engaging the in-tube rib 12 and the L-shape vertical rib 38. Methods of releasing the joint preventing means are as follows. In the case of FIG. 2(a), the joint preventing means is released by removing the distal direction movement preventing member 9. In the case of FIG. 2(b), the joint preventing means is released by breaking the projection 34 at a separating portion 341. In the case of FIG. 2(c), the joint preventing means is released by pulling the plunger 3 and simultaneously lifting the elastic projection 35 toward the outer periphery of the plunger 3 so that the elastic projection 35 and the annular rib 13 are disengaged and the elastic projection 35 is moved to be fit within the largest width of the plunger 3. In FIG. 3, the joint preventing means 90 is released by rotating the plunger 3 until the in-tube rib 12 is disengaged with the L-shape vertical rib 38. It is also possible that the plunger cannot be moved in any direction until the joint preventing means is released. However, since it is possible to operate without actuating the joint preventing means until drug solution is completely drawn from a vial, that is, until immediately before use by limiting only forward movement of the gasket as shown in FIGS. 2(a) to (c) and FIG. 3, there is no probability of operation by mistake such that the joint preventing means is released before drawing and is pushed toward the front. Therefore, the plunger does not have to be the shape having vertical ribs in a cross-shape, and in a case where the shape of the plunger is changed, the shape of the joint preventing means may also be changed according to the shape of the plunger.

In an immovable state of the plunger toward the distal end of the injection barrel provided by the joint preventing means 90, the length of the plunger which extends out from the injection barrel 1 is set to be longer than that of the plunger which extends out from the injection barrel 1 when the plunger 3 is pushed toward the distal end of the injection barrel to the end. In other words, in order to prevent the plunger and the needle body from joining to each other, the needle body and the gasket 2 are kept out of contact by the joint preventing means 90.

Although the joint preventing means 90 is provided on the plunger as shown above, it may be formed either on the injection barrel 1 or the plunger 3. For example, a separable projection is formed on the proximal surface of the finger mount portion 14 so as to contact with the distal surface of the flange 36, an annular rib is formed on the distal surface of the flange 36 and an elastic projection capable of engaging the annular rib and having a free end on the proximal side is formed on the proximal surface of the finger mount portion 14, and the distal direction movement preventing member for preventing forward movement of the plunger attached to the injection barrel 1, are also applicable.

The shape and the material of the joined means 61 provided on the proximal end of the needle base 6 are not specifically limited as long as the joined means 61 can be joined with the joining means 21 of the gasket 2 and is not separated from the needle base 6 during storage and use. Therefore, it is acceptable that the needle base 6 and the joined means 61 are formed integrally, and the needle base 6 and the joined means 61 are formed separately and the needle base 6 is connected to the joined means 61.

A method of coupling the needle base lid member 7 with the connecting portion 11 is not specifically limited, and they may be fitted by covering the proximal end of the needle base lid member 7 on the connecting portion 11, or may be engaged by a thread groove formed on the connecting portion 11 and a thread formed inside the needle base lid member 7 so as to be engaged with the screw groove on the connecting portion 11, or may be attached by a luer-lock system in which the connecting portion 11 is formed into a double-cylinder shape having a female thread on the inner side of the outer tube and the needle base lid member 7 is equipped with a projection which is capable of engaging with the female screw so that the needle base lid member is screwed into the connecting portion 11.

Referring now to FIG. 3, a method of usage of the safety syringe of the invention until administration of drug solution will be described. After having connected the needle assembly B to the connecting portion 11, the plunger is pulled toward the proximal end without removing the distal direction movement preventing member 9 from the plunger 3, and drug solution 15 is drawn from an ampoule or the like. Then, the distal direction movement preventing member 9 is removed from the plunger 3 and the drug solution 15 is administrated to a human body. In particular, when connecting the needle assembly B to the connecting portion 11 or drawing the drug solution 15 from the ampoule, there is a probability that a force pushing the plunger 3 is applied unintentionally, and hence the gasket 2 is moved toward the distal end of the injection barrel so the gasket 2 is connected to the needle body. However, since the distal direction movement preventing member 9 is fitted to the vertical ribs 37 of the plunger 3 and both ends of it are in contact with the proximal surface of the finger mount portion 14 of the injection barrel 1 and the distal surface of the flange 36 of the plunger 3 to prevent movement of the plunger 3 toward the distal end of the injection barrel, there is no probability that the gasket 2 is connected to the needle body. In addition, since the needle body is prevented from moving toward the proximal end by engagement of the upper claws 62 and the rib 111, and is prevented from moving toward the distal end by fitting of the distal end of the needle base 6 to the needle base fitting portion 71 of the needle base lid member 7, the probabilities that the needle body is retracted into the injection barrel when being pricked into the human body, and that the needle body is separated from the syringe after having been pricked into the human body and stays in the human body are avoided. Furthermore, when drawing the drug solution, the needle base 6 of the needle body is in a state of being fitted to the needle base fitting portion 71 at the distal end of the needle base lid member 7, and hence the distal end of the needle base lid member 7 is closed. Therefore, liquid is prevented from leaking through the needle base lid member 7. In addition, since the gasket is equipped with the bulkhead portion, there is no probability of leakage of the liquid toward the proximal end of the gasket, so the liquid does not flow into and flow out from the injection syringe other than through the injection needle 5.

Referring to FIG. 5, a method of handling the safety syringe of the invention after having administered the drug solution will be described. The injection needle 5 is pulled out from the patient, the plunger 3 is pushed toward the distal end of the injection barrel 1, the tube body 211 of the gasket 2 enters into the flow channel of the connecting portion 11, the tube body 211 of the gasket is press-contact with the lower claws 63 as the joined means 61, and the lower claws 63 are engaged with the rib of the tube body 211 formed on the gasket. Consequently, the distance between right claw and left claw is reduced, and hence the upper claws 62 of the needle body are released from the rib 111 formed on the connecting portion 11 of the injection barrel 1, whereby the needle body and the gasket 2 are integrated and then the needle body is able to be slidable together with the gasket 2. Then, the plunger 3 is pulled, the needle body and the gasket 2 are stored in the interior of the injection barrel 1, the plunger 3 is broken at the notch 331 which is the separating means 33, and the plunger 2 is separated from the gasket 30. By using the safety syringe of the invention, the engagement of the needle body and the injection barrel is released, and the gasket and the needle body are engaged by pushing the plunger inward and bringing the gasket into press-contact with the needle body, and hence the gasket and the needle body can be operated. Then, sliding movement of the gasket is disabled by separating the plunger from the gasket by the separating means, and hence the gasket and the needle body engaged with the gasket remain in the injection barrel, so that the injection syringe can be discarded safely. In the case where the engagement of the gasket and the plunger is screwing, in particular, the coupled portion also serves as the separating means and therefore the gasket can be separated from the plunger by releasing screwing.

The connecting method of the joining means 21 of the gasket 2 and the joined means 61 of the needle body is not specifically limited as long as the joining means 21 is connected to the joined means 61 by pushing the gasket 2 toward the distal end of the injection barrel 1 and bringing the gasket 2 into contact with the joined means 61 of the needle body, the connecting portion 11 is released from the needle body, and hence the needle body and the gasket 2 can be stored in the interior of the injection barrel 1. In some cases, a structure other than the rib 111 may be provided on the connecting portion 11, or the connecting portion 11 with nothing provided thereon is also applicable. For example, a magnetic member is provided as the joining means 21 of the gasket 2 and the joined means 61 of the needle body, which have a force of sticking to each other when press contacted.

INDUSTRIAL APPLICABILITY

As described above, the syringe of the invention is provided with the joint preventing means, and hence the gasket does not come into contact with the distal end of the injection barrel unless the joint preventing means is released, and hence the joining means and the joined means are not joined to each other. Therefore, the gasket and the needle body are prevented from being connected with each other and becoming unusable before using the injection syringe. In addition, since the sliding movement of the gasket in the axial direction is enabled by releasing the joint preventing means, the needle storage mechanism can be operated, and the needle is stored into the injection barrel after use, so puncture by mistake is avoided. In addition, the needle is prevented from being exposed again by separating the plunger and the gasket, so the syringe of the invention is suitably used for medical practice.

The invention claimed is:

1. A safety syringe including: a hollow and substantially cylindrical injection barrel having a distal end and a proximal end and having a connecting portion at the distal end and an opening at the proximal end thereof; a needle assembly including an injection needle and a needle base, the injection needle having a distal end and a proximal end, the needle base having a distal end and a proximal end, and the needle base being fixed to the proximal end of the injection needle and being connected to the connecting portion of the injection barrel; a gasket provided liquid-tightly and slidably in the injection barrel, the gasket having a distal end and a proximal end; a plunger being connected to the proximal end of the gasket, the plunger having a distal end and a proximal end and being rotatable in the injection barrel; joining means provided at the distal end of the gasket or the distal end of the plunger; and joined means provided at the proximal end of the needle base;

the safety syringe further comprising a joint preventing means, which prevents only movement of the plunger toward the distal end of the injection barrel and allows movement of the plunger toward the proximal end of the injection barrel, whereby the joining means and the joined means are prevented from being joined unintentionally before use, and are allowed to be joined to each other when in use, the joint preventing means including an engaging portion provided in an interior of the proximal end of the injection barrel and an engaged portion provided at a midsection of the plunger, and the engaging portion and the engaged portion being engaged before use and disengaged during use; wherein the engaging portion provided in the interior of the proximal end of the injection barrel is an engaging rib provided on a portion of an inner wall of the injection barrel and the engaged portion is a proximal end of an L-shape vertical rib provided on the plunger, the L-shaped vertical rib being engaged with the engaging rib in a first position of the rotatable plunger prior to use and disengaged with the engaging rib in a second rotated position of the rotatable plunger during use.

* * * * *